(12) United States Patent
Fukaya et al.

(10) Patent No.: US 8,507,858 B2
(45) Date of Patent: Aug. 13, 2013

(54) PATTERN MEASUREMENT APPARATUS AND PATTERN MEASUREMENT METHOD

(71) Applicant: Advantest Corporation, Tokyo (JP)

(72) Inventors: Hiroshi Fukaya, Tokyo (JP); Yoshiaki Ogiso, Tokyo (JP)

(73) Assignee: Advantest Corp., Tokyo (JP)

( * ) Notice: Subject to any disclaimer, the term of this patent is extended or adjusted under 35 U.S.C. 154(b) by 0 days.

(21) Appl. No.: 13/652,110

(22) Filed: Oct. 15, 2012

(65) Prior Publication Data

US 2013/0105691 A1 May 2, 2013

(30) Foreign Application Priority Data

Oct. 26, 2011 (JP) .................................. 2011-234546

(51) Int. Cl.
*H01J 37/26* (2006.01)
*H01J 37/28* (2006.01)
*H01J 37/244* (2006.01)

(52) U.S. Cl.
USPC ........... 250/310; 250/306; 250/307; 250/397; 382/286; 382/199

(58) Field of Classification Search
USPC ................. 250/310, 306, 307, 397; 382/286, 382/199
See application file for complete search history.

(56) References Cited

U.S. PATENT DOCUMENTS 8,431,895 B2 * 4/2013 Matsumoto et al. .......... 250/307
2012/0112066 A1 * 5/2012 Ogiso et al. .................... 250/307
2012/0318976 A1 * 12/2012 Matsumoto et al. .......... 250/307

FOREIGN PATENT DOCUMENTS

JP        2011-169835        9/2011

* cited by examiner

*Primary Examiner* — Nikita Wells
(74) *Attorney, Agent, or Firm* — Muramatsu & Associates

(57) ABSTRACT

Referring to design data for a sample, a measurement region is defined at a portion in the design data which has no step in an edge of a pattern. In addition, an edge as a characteristic portion is detected from the design data, and an edge as a characteristic portion corresponding to the characteristic portion of the design data is detected from a secondary electron image. Then, the measurement region is positioned and located in a secondary electron image based on a positional relationship between the edge of the design data and the edge of the secondary electron image. A width of the pattern is measured on the basis of a distance between the two edges included in the measurement region thus located.

16 Claims, 20 Drawing Sheets

| space width (μm) | 0.1 | 0.2 | 0.3 | 0.4 | 0.5 | 小計 |
|---|---|---|---|---|---|---|
| 0.1 | 0 | 0 | 18 | 0 | 0 | 18 |
| 0.2 | 0 | 2 | 14 | 0 | 3 | 19 |
| 0.3 | 0 | 1 | 2 | 0 | 0 | 3 |
| ⋮ | ⋮ | ⋮ | ⋮ | ⋮ | ⋮ | ⋮ |
| 2.3 | 1 | 0 | 0 | 0 | 0 | 1 |

(space length (μm) labels the rows)

PATTERN MEASUREMENT APPARATUS AND PATTERN MEASUREMENT METHOD

CROSS-REFERENCE TO RELATED APPLICATIONS

This application is based upon and claims and the benefit of priority of the prior Japanese Patent Application No. 2011-234546, filed on Oct. 26, 2011, the entire contents of which are incorporated herein by reference.

BACKGROUND OF THE INVENTION

1. Field of the Invention

The embodiments discussed herein are related to a pattern measurement apparatus and a pattern measurement method, which are configured to measure a pattern by irradiating a surface of a sample with an electron beam.

2. Description of Related Art

Along with miniaturization of semiconductor devices in recent years, an OPC (Optical Proximity effect Correction) mask formed in consideration of optical proximity effect is used in a photolithography process for semiconductor devices. Such an OPC mask requires high precision, and therefore an actually produced OPC mask undergoes a measurement for checking whether or not the mask exactly has a line width as designed.

Conventionally, a line width of a pattern is found by referring to a secondary electron image of the pattern, defining a rectangular measurement region called a ROI (Region of Interest) in such a way as to intersect the pattern, and then measuring a distance between edges of the pattern in the measurement region. The line width cannot be measured precisely if a corner of the pattern is included in the measurement region. Accordingly, the measurement region is defined to selectively include a straight-line portion of the pattern.

In the meantime, since a pattern of an OPC mask is formed by connecting a plurality of small patterns (blocks) to one another in design data, a stepped portion may be formed at a joint between the small patterns. For this reason, even a portion which appears to be a straight-line portion in the secondary electron image may be formed as a small stepped portion in the design data. As a consequence, it is not always possible to measure a line width precisely in a measurement region defined to include a straight-line portion picked up based only on the secondary electron image.

PATENT DOCUMENT

Japanese Laid-open Patent Publication No. 2011-169835

SUMMARY OF THE INVENTION

An object of the present invention is to provide a pattern measurement apparatus and a pattern measurement method, which enable precise measurement of a line width of a pattern.

According to an aspect of the disclosure below, a pattern measurement apparatus is provided which includes: an electron beam irradiation unit configured to irradiate a surface of a sample with an electron beam; a detector configured to detect secondary electrons generated on the surface of the sample; a signal processor configured to create a secondary electron image of the surface of the sample based on a detection signal from the detector; a measurement region definition unit configured to define a measurement region in design data while referring to the design data for the sample; a first detection unit configured to detect a characteristic portion of the design data; a second detection unit configured to detect a characteristic portion of the secondary electron image; an alignment unit configured to position and locate the measurement region of the design data in the secondary electron image based on a positional relationship between the characteristic portion of the design data and the characteristic portion of the secondary electron image; and a measurement unit configured to measure a width of a pattern inside the measurement region of the secondary electron image based on positions of edges of the pattern.

Further, according to another aspect of the disclosure, a pattern measurement method for defining a measurement region in a secondary electron image and finding a line width of a pattern in the measurement region using positions of edges of the pattern is provided, the method including the steps of: defining a measurement region in design data corresponding to a field of view of the secondary electron image; detecting a characteristic portion of the design data; detecting a characteristic portion of the secondary electron image; and positioning and locating the measurement region of the design data in the secondary electron image based on a positional relationship between the characteristic portion of the design data and the characteristic portion of the secondary electron image.

According to the above-described aspects, the measurement region is defined while referring to the design data and the measurement region is positioned and located in the secondary electron image based on the positional relationship between the characteristic portion in the design data and the characteristic portion in the secondary electron image. In this way, the measurement region defined on the basis of the design data can be located in the secondary electron image at the same position as in the design data. Thus, a line width of a pattern can be measured more precisely.

DETAILED DESCRIPTION OF THE EMBODIMENTS

A prelude forming the basis of the invention will be explained prior to description of embodiments.

Figure 1A:
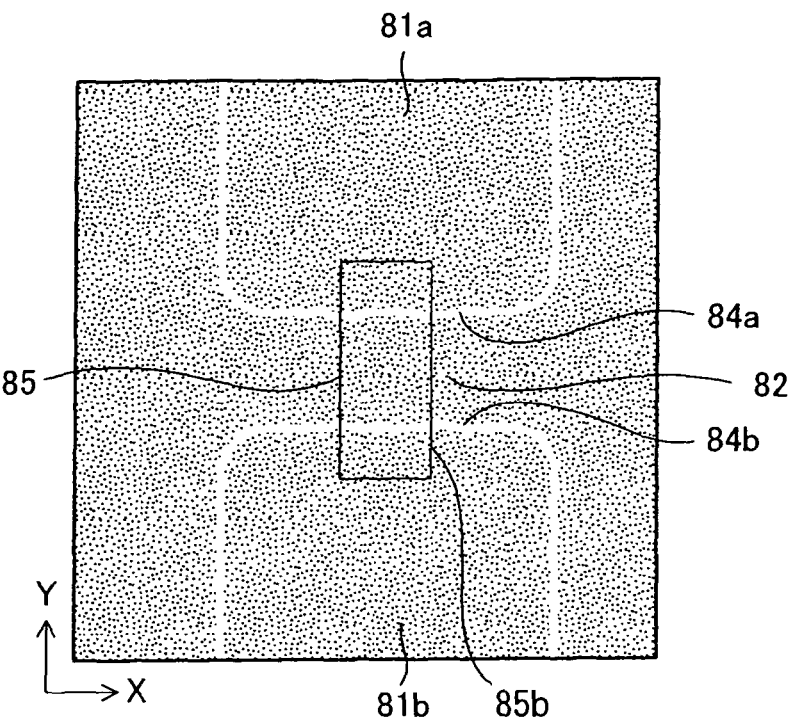
FIG. 1A is a view illustrating an example of definition of a measurement region based on a secondary electron image and FIG. 1B is a view illustrating design data of a portion corresponding to FIG. 1A.
Figure 1B:
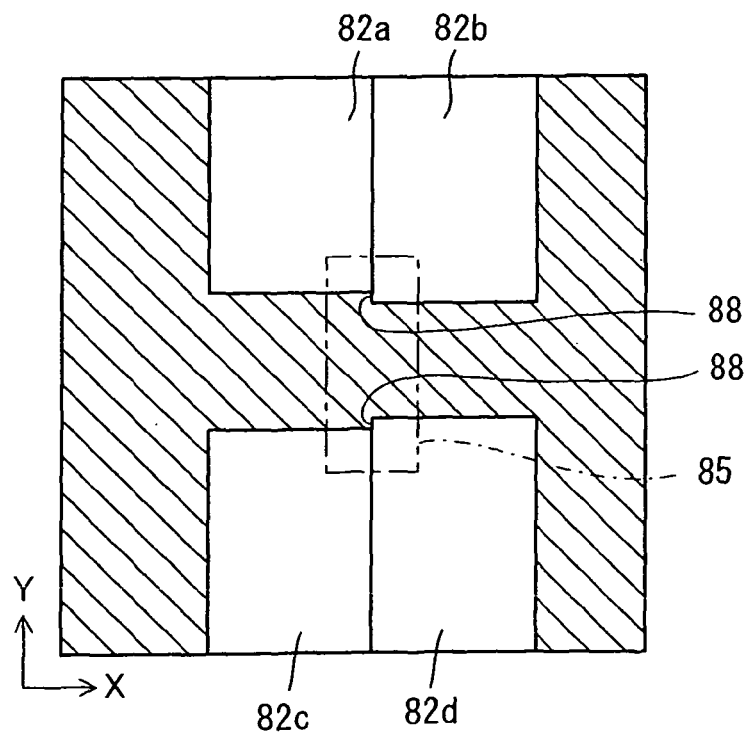

FIG. 1A is a view illustrating an example of definition of a measurement region based on a secondary electron image and FIG. 1B is a view illustrating design data of a portion corresponding to FIG. 1A.

Patterns 81a and 81b and a space 82 are formed in a field of view of the secondary electron image in FIG. 1A, and band-like edges 84a and 84b each called a white band and having higher luminance than the remaining portions appear at border portions between the patterns and the space.

In the case of measuring a width of the space 82 near the center of the drawing, a rectangular measurement region 85 called a ROI (Region of Interest) is defined to include the edges 84a and 84b of the patterns 81a and 81b. Next, a line profile representing distribution of luminance values of the secondary electron image along a line extending in a width direction (a Y direction) is found within the measurement region 85. Then, the width of the space 82 is found by measuring a distance between points of local maximum luminance values in the line profile.

In the meantime, since a pattern of an OPC mask is formed by connecting small patterns (blocks) 82a and 82b (or 82c and 82d) to each other in design data, a stepped portion may be formed at a joint between the blocks. For this reason, in reference to the design data as illustrated in FIG. 1B, it might be found that a small stepped portion 88 is formed at a portion which appears to be a straight-line portion in the secondary electron image.

According to a research conducted by the inventors of the present application, a stepped portion in a size of about several nanometers in the design data cannot be detected in the secondary electron image. Thus, it turned out to be difficult to avoid the stepped portion 88 in the design data in the case of a measurement based only on the secondary electron image. As a consequence, a stepped portion may be included in the measurement region, which hinders a precise measurement of the line width.

Based on the knowledge mentioned above, the inventors of the present application have conceived of the following embodiments.

First Embodiment

Figure 2:
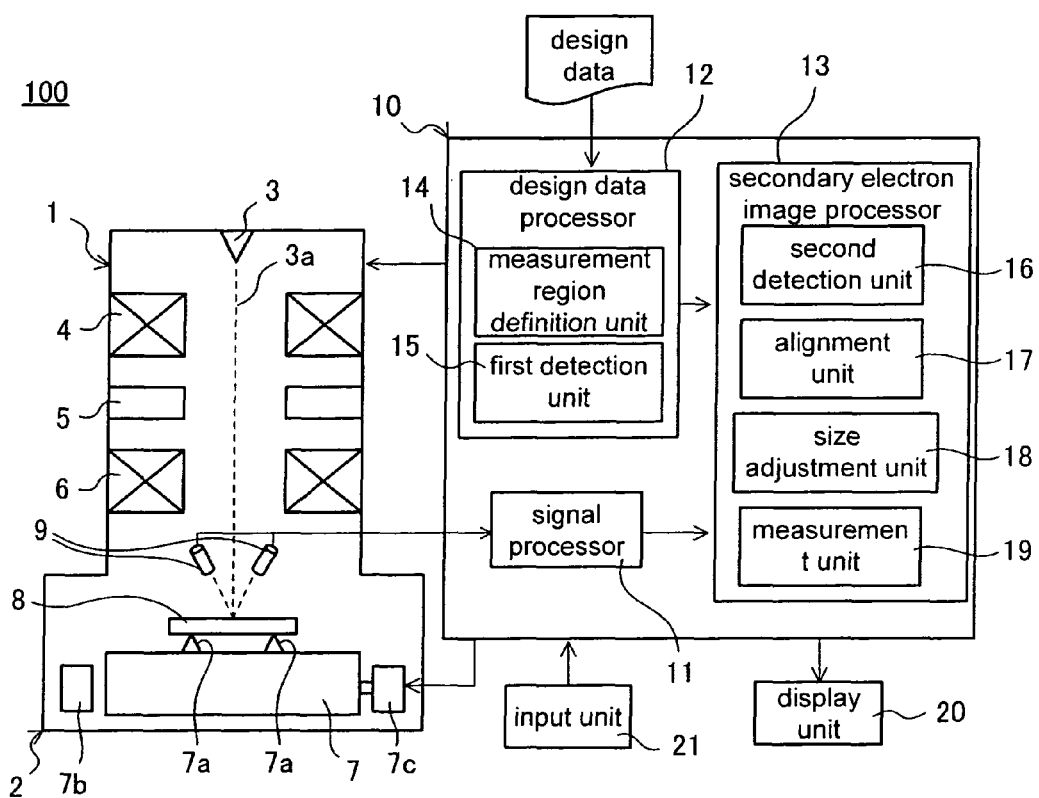
FIG. 2 is a block diagram of a pattern measurement apparatus according to a first embodiment.

FIG. 2 is a block diagram of a pattern measurement apparatus according to a first embodiment.

As illustrated in FIG. 2, a pattern measurement apparatus 100 of this embodiment includes a chamber 2 configured to house a sample 8, an electronic scanning unit 1 configured to irradiate the sample 8 with an electron beam, and a controller 10 configured to control the electronic scanning unit 1 and the chamber 2 and to perform data processing.

A stage 7 with support bodies 7a on its upper part is installed in the chamber 2 and the sample 8 such as a wafer or a photomask is held on the support bodies 7a. The stage 7 is driven by a drive unit 7c to move the sample 8 to a predetermined position while its position is measured with a laser interferometer 7b. Meanwhile, a positioning mark is formed on a surface of the sample 8 so that positional coordinates of the sample 8 can be determined by observing the positioning mark.

An electron beam 3a is emitted from an electron gun 3 of the electronic scanning unit 1. The electron beam 3a is condensed by a condenser lens 4 and is then projected onto the surface of the sample 8 through an object lens 6 while being deflected in a scanning manner using a deflecting coil 5. Secondary electrons which are emitted from the surface of the sample 8 as a consequence of irradiation with the electron beam 3a are detected by detectors 9 and are converted into electric signals.

The controller 10 outputs control signals to the respective components in the electronic scanning unit 1 and the chamber 2 described above.

The controller 10 includes a signal processor 11, a design data processor 12, and a secondary electron image processor 13. Among them, the signal processor 11 converts analog signals from the detectors 9 into digital signals, and creates a secondary electron image which indicates detected amounts of secondary electrons in respective positions irradiated with the electron beam in the form of luminance.

The design data processor 12 includes a measurement region definition unit 14 and a first detection unit 15. The measurement region definition unit 14 extracts a portion of design data corresponding to a field of view of a secondary electron image and defines a rectangular measurement region at a portion of the extracted design data where stepped portions or corners of a pattern are not present. Meanwhile, the first detection unit 15 detects a characteristic portion from a pattern of the design data in order to position the measurement region. An edge or a corner of the pattern is detected as the characteristic portion.

The secondary electron image processor 13 performs measurement of a pattern in the sample 8 by processing a secondary electron image using a second detection unit 16, an alignment unit 17, a size adjustment unit 18, and a measurement unit 19. Among them, the second detection unit 16 detects a characteristic portion from the pattern of the secondary electron image in order to position the measurement region. An edge of the pattern or an inflection point of the edge is detected as the characteristic portion.

Meanwhile, the alignment unit 17 positions and locates the measurement region of the design data in the secondary electron image on the basis of a positional relationship between the characteristic portion in the secondary electron image and the characteristic portion in the design data. In addition, when a curved portion in the vicinity of a corner of the pattern of the secondary electron image is included in the measurement region located by the alignment unit 17, the size adjustment unit 18 adjusts the size of the measurement region so as to exclude the curved portion from the measurement region.

The measurement unit 19 finds a line profile of the measurement region located in the secondary electron image, and measures and obtains a distance between points of local maximum luminance values on the line profile as a line width of the pattern.

Moreover, a display unit 20 and an input unit 21 are connected to the above-described controller 10. Secondary electron images and the like are displayed on the display unit 20. Meanwhile, measurement conditions and the like are inputted from the input unit 21.

Now, a pattern measurement method using the pattern measurement apparatus 100 will be described below.

Figure 3:
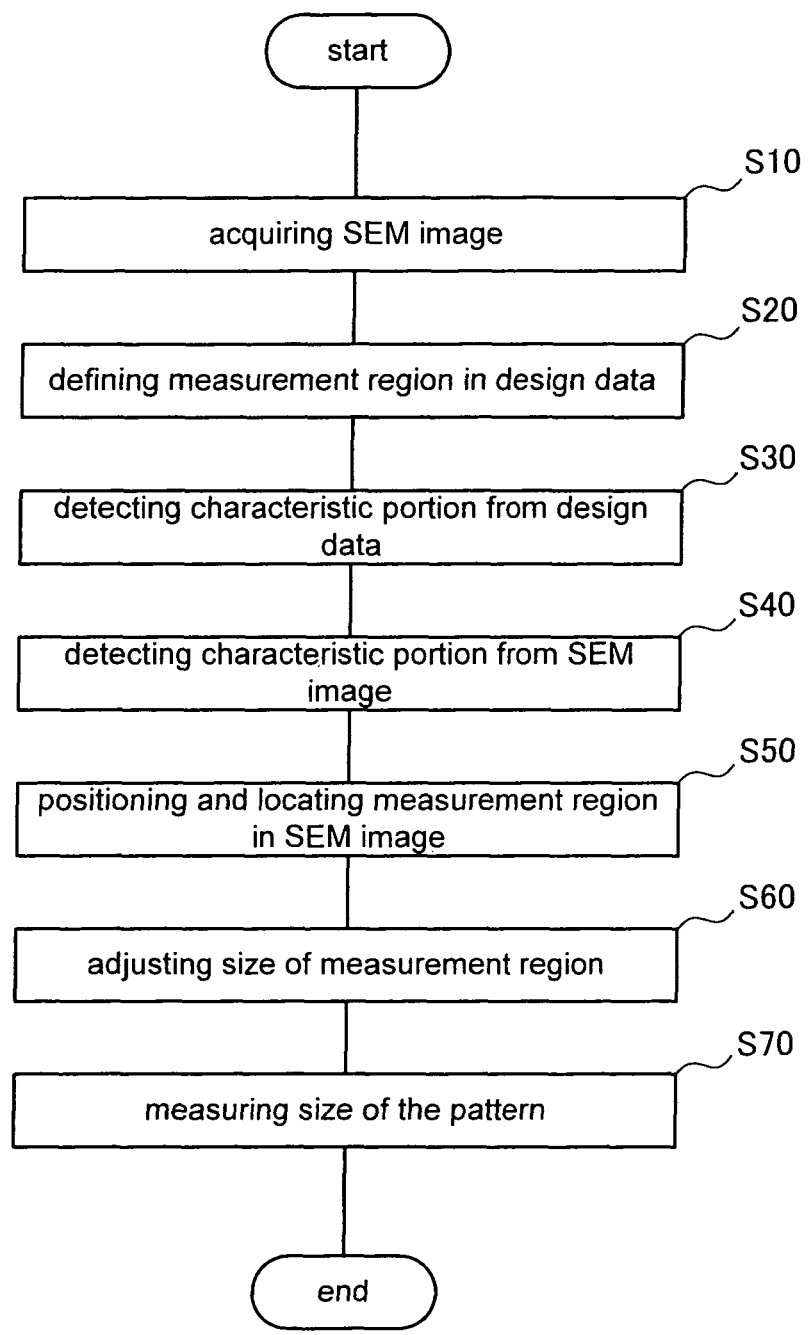
FIG. 3 is a flowchart illustrating showing a pattern measurement method using the pattern measurement apparatus of FIG. 2.

FIG. 3 is a flowchart illustrating the pattern measurement method of this embodiment.

First, in step S10 of FIG. 3, a secondary electron image of a surface of the sample 8 is acquired by the pattern measurement apparatus 100 (see FIG. 2).

Next, in step S20, the measurement region definition unit 14 (see FIG. 2) of the design data processor 12 refers to design data and defines a measurement region at a portion where stepped portions or corners of a pattern are not present.

Figure 4A:
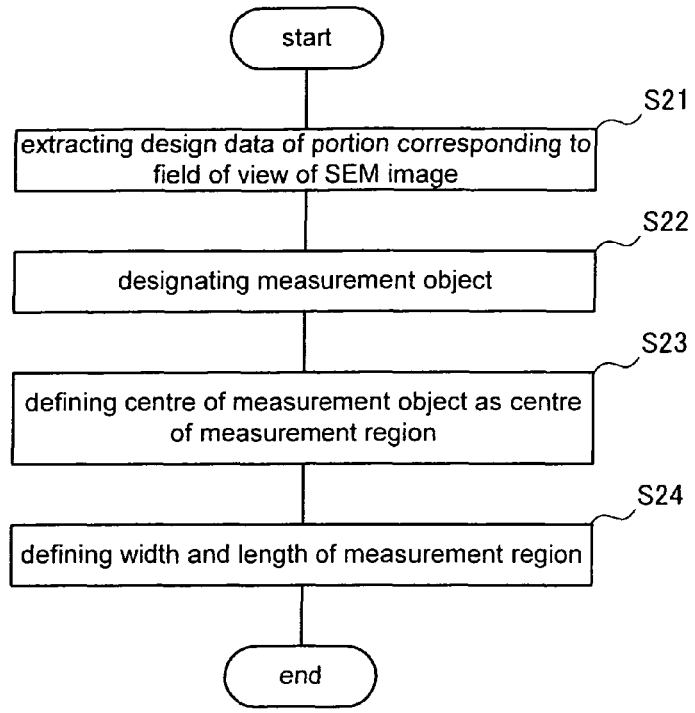
FIG. 4A is a flowchart illustrating a method of defining a measurement region in design data according to the first embodiment and FIG. 4B is a view illustrating an example of the measurement region defined in the design data with the method of FIG. 4A.
Figure 4B:
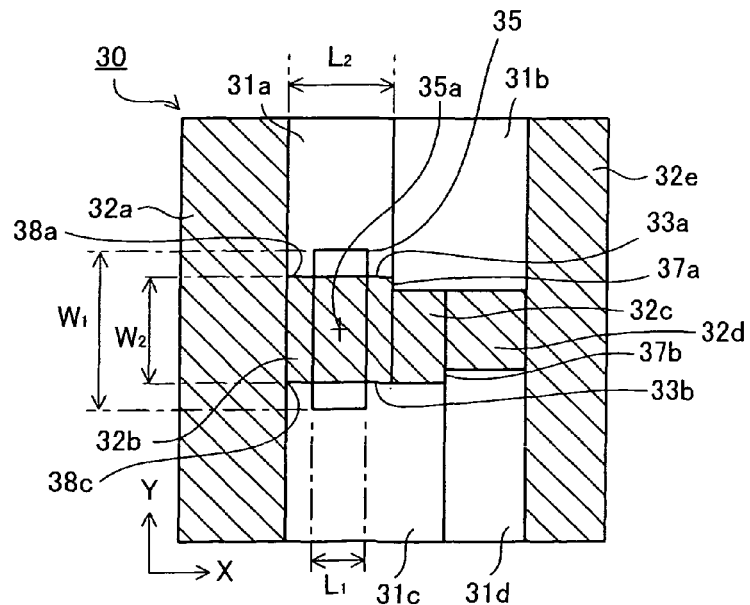

FIG. 4A is a flowchart illustrating a method of defining a measurement region by the measurement region definition unit 14 of this embodiment and FIG. 4B is a view illustrating an example of the measurement region defined with the method of FIG. 4A.

First, in step S21 of FIG. 4A, the measurement region definition unit 14 extracts the design data of a portion corresponding to a field of view of the secondary electron image. In this case, design data 30 as illustrated in FIG. 4B is assumed to be extracted. Here, in the design data 30, patterns and spaces are formed by joining a plurality of rectangular blocks 31a to 31d and 32a to 32e, and stepped portions 37a and 37b are present at joints of the blocks. The design data 30 extracted in this step is displayed on a display screen of the display unit 20.

Subsequently, in step S22 of FIG. 4A, the measurement region definition unit 14 designates an object to be measured (a block, hereinafter referred to as a measurement object) where a measurement region 35 is to be located.

Here, when an operator selects a certain portion in the design data 30 based on the design data 30 of FIG. 4B displayed on the display unit 20, the measurement region definition unit 14 detects the selected block and defines the detected block as the measurement object.

In FIG. 4B, the block 32b is assumed to be designated as the block serving as the measurement object.

Next, in step S23 of FIG. 4A, the measurement region definition unit 14 defines the center of the block serving as the measurement object, as the center of the measurement region. For example, in the case of FIG. 4B, coordinates of the center of the block 32b are defined as coordinates of the center 35a of the measurement region 35.

Next, in step S24 of FIG. 4A, the measurement region definition unit 14 defines a width and a length of the measurement region 35.

Here, as illustrated in FIG. 4B, the measurement region definition unit 14 detects two edges 33a and 33b of the block 32b serving as the measurement object, then defines a direction orthogonal to the edges 33a and 33b (a Y direction in FIG. 4B) as a width direction of the measurement region 35 and defines a direction parallel to the edges 33a and 33b (an X direction in FIG. 4B) as a length direction of the measurement region 35.

Next, the measurement region definition unit 14 finds an interval $W_2$ between the edges 33a and 33b and defines a width $W_1$ larger than the interval $W_2$ as the width of the measurement region 35. The width $W_1$ may be set about 1.5 times as large as the width $W_2$ of the block 32b, for example.

Subsequently, the measurement region definition unit 14 finds a length $L_2$ of the block 32b and defines a length $L_1$ smaller than the length $L_2$ as the length of the measurement region 35. Here, the length $L_1$ may be set equal to or below 0.9 times as large as the length $L_2$ of the block 32b, for example. As described above, the measurement region 35 can be defined at the portion not including the stepped portions 37a and 37b as well as corners 38a and 38b by aligning the center of the measurement region 35 with the center of the block 32b and defining the length $L_1$ of the measurement region 35 smaller than the length $L_2$ of the block 32b.

Thus, the definition of the measurement region 35 in the design data 30 is completed.

In the meantime, the following problem may arise when the measurement region 35 defined in the design data 30 is located in the secondary electron image without any change.

Figure 5:
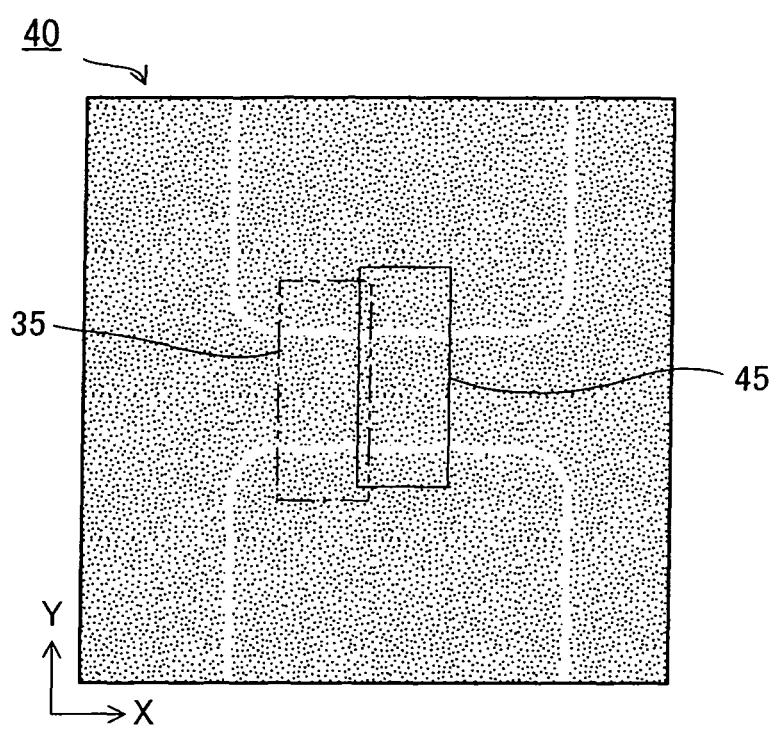
FIG. 5 is a view illustrating an example of locating the measurement region, which is defined in the design data, onto a secondary electron image without positioning.

FIG. 5 is a view illustrating a problem in the case of locating the measurement region, which is defined in the design data, in the secondary electron image. In FIG. 5, a section indicated with a chain line is a position to locate the measurement region 35 intended in the design data 30 and a section indicated with a solid line shows a position of a measurement region 45 located on a secondary electron image 40 by using coordinates of the measurement region 35 of the design data 30 without any change.

As illustrated in FIG. 5, when the measurement region 35 defined in the design data 30 is located in the secondary electron image 40 without positioning, the position of the measurement region 45 in the secondary electron image 40 is displaced from the position of the measurement region 35 intended in the design data 30. It is likely that such displacement between the measurement region 35 and the measurement region 45 is attributable to an error associated with detection of the position of the stage 7 using the laser interferometer 7b of the pattern measurement apparatus 100, for instance.

As a consequence, it is not always possible to locate the measurement region 45 at the portion including no stepped portions or corners when the measurement region 35 is located in the secondary electron image 40 without positioning.

Accordingly, the pattern measurement method of this embodiment performs positioning of the measurement region in step S30 to step S50 of FIG. 3.

First, in step S30, the first detection unit 15 (see FIG. 2) of the design data processor 12 detects the characteristic portion of the pattern in the design data. The characteristic portion serves as a mark for positioning the measurement region in the secondary electron image. Here, an edge or a corner of the pattern in the design data is detected as the characteristic portion.

Now, a method of detecting a characteristic portion will be concretely described.

Figure 6:
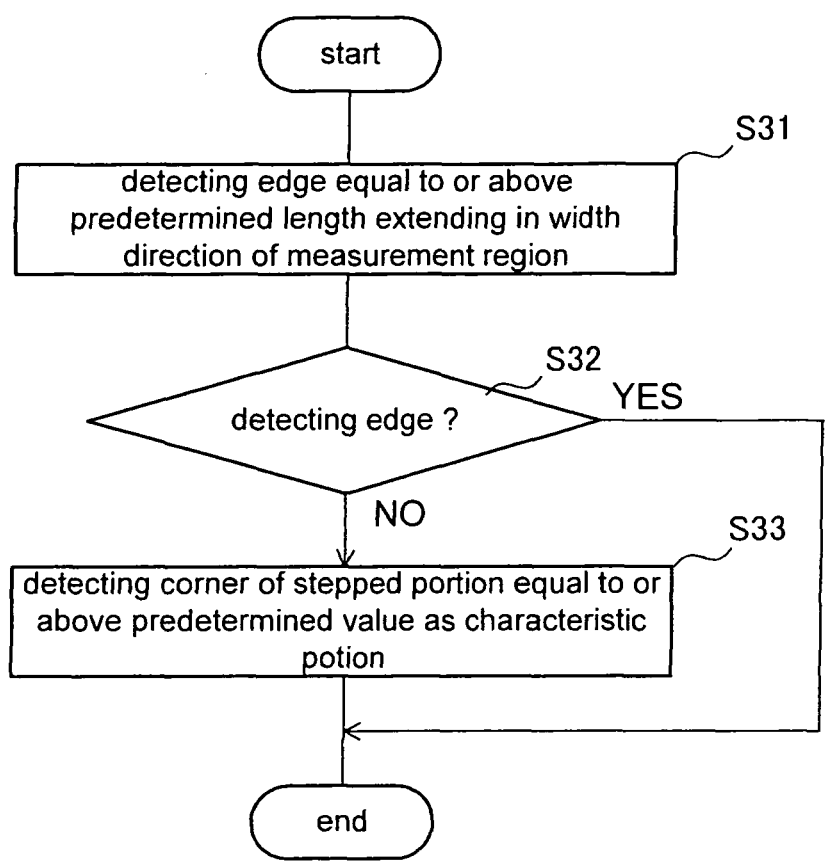
FIG. 6 is a flowchart illustrating a method of detecting a characteristic portion in the design data in the pattern measurement method according to the first embodiment.

FIG. 6 is a flowchart illustrating the method of detecting a characteristic portion in design data using the first detection unit 15 of this embodiment. Meanwhile, FIG. 7A is a view illustrating an example in which edges of a pattern in design data are detected as characteristic portions and FIG. 7B is a view illustrating an example in which corners of the pattern in the design data are detected as characteristic portions.

First, in step S31 of FIG. 6, the first detection unit 15 of the design data processor 12 refers to the pattern of the design data and detects edges having a length equal to or above a predetermined value from edges extending in the width direction of the measurement region. Here, edges having a length equal to or above 25 nm are assumed to be detected.

Figure 7A:
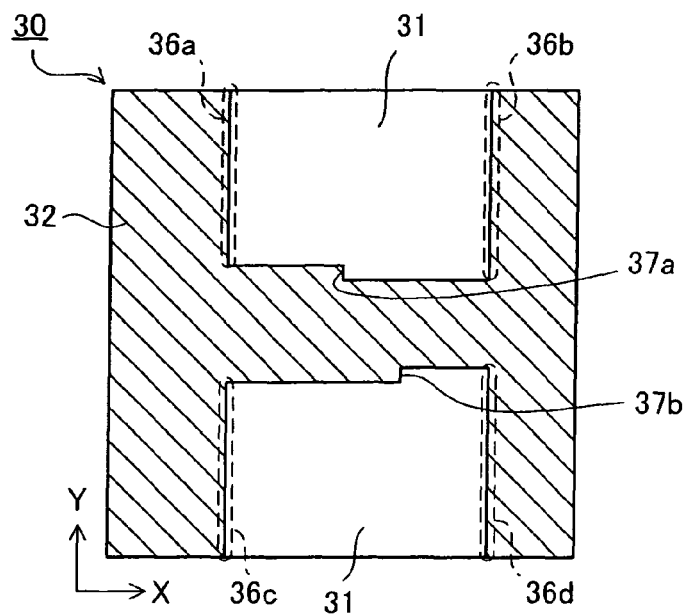
FIG. 7A is a view illustrating an example in which edges are detected as characteristic portions from design data in the first embodiment and FIG. 7B is a view illustrating an example in which corners are detected as characteristic portions from the design data in the first embodiment.
Figure 7B:
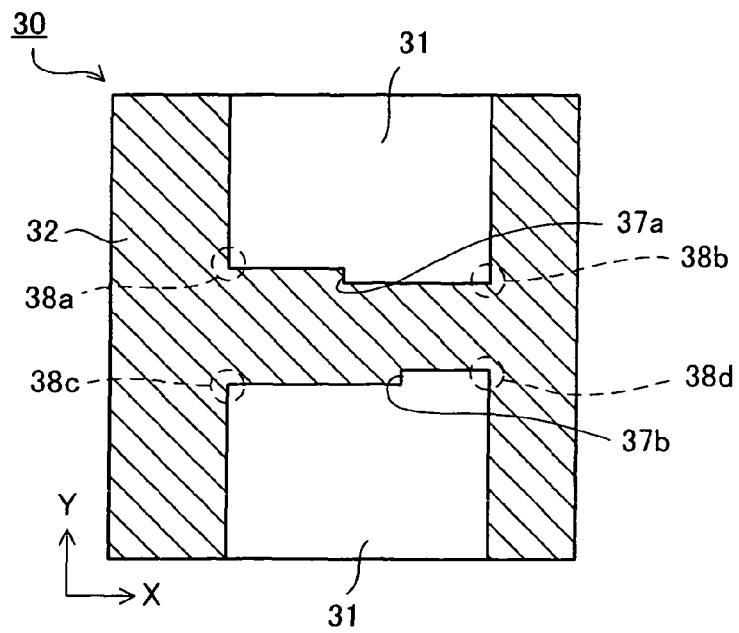

In the case of the design data 30 of FIG. 7A, for example, the first detection unit 15 detects edges 36*a*, 36*b*, 36*c*, and 36*d* extending in the width direction (the Y direction) of the measurement region 35 as the characteristic portions. In the case of the edges 36*a* to 36*d* each having a length equal to or above 25 nm and extending in the width direction in the design data, corresponding edges can be detected easily in the secondary electron image. In addition, positions of the edges in the length direction of the secondary electron image (the X direction in FIG. 7A) can be accurately determined. Accordingly, the edges 36*a* to 36*d* are suitable for the characteristic portions for positioning the measurement region 35 in the length direction.

On the other hand, edges having a length below 25 nm as edges of the stepped portions 37*a* and 37*b* may result in a failure in reliable detection of corresponding edges in the secondary electron image. For this reason, the edges of the stepped portions 37*a* and 37*b* are excluded from the objects to be detected in step S31.

Next, in step S32 of FIG. 6, a judgment is made as to whether or not the first detection unit 15 has detected any edges in step S31. When a judgment is made that the edges have been detected (YES), the processing for detecting the characteristic portions of the design data is terminated.

On the other hand, no edges may be detected in step S31 depending on the pattern. In such a case, a judgment turns out to be NO in step S32 and the processing goes to the next step S33.

In step S33, the first detection unit 15 detects corners of stepped portions having a size equal to or above a predetermined value as the characteristic portions. Here, corners of the stepped portions having a size equal to or above 5 nm are assumed to be detected as the characteristic portions.

In the design data 30 illustrated in FIG. 7B, the first detection unit 15 detects corners 38*a*, 38*b*, 38*c*, and 38*d* of a pattern 31. It is to be noted, however, that a corner of a small stepped portion having a size equal to or below 5 nm like the stepped portions 37*a* and 37*b* may result in a failure in reliable detection of the corresponding characteristic portion in the secondary electron image. For this reason, the corners of the stepped portions 37*a* and 37*b* are excluded from the objects to be detected in step S33.

Thus, detection of the characteristic portions from the design data is completed.

Next, in step S40 of FIG. 3, the second detection unit 16 (see FIG. 2) of the secondary electron image processor 13 detects characteristic portions of a pattern on a secondary electron image.

Figure 8A:
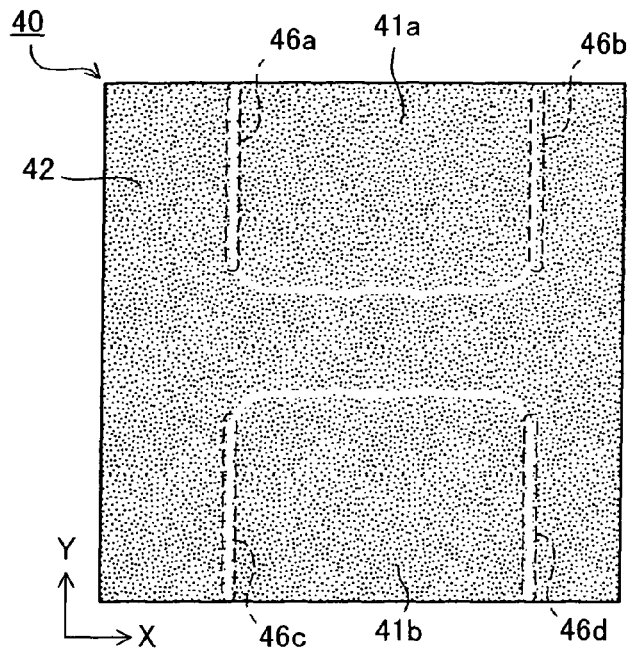
FIG. 8A is a view illustrating an example in which edges are detected as characteristic portions from a secondary electron image in the first embodiment and FIG. 8B is a view illustrating an example in which inflection points of the edges are detected as characteristic portions from the secondary electron image in the first embodiment.
Figure 8B:
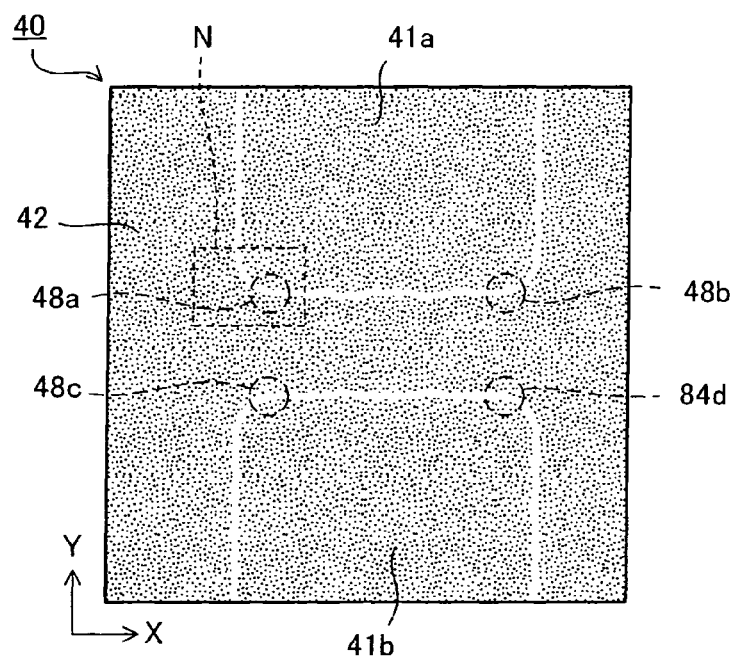

FIG. 8A is a view illustrating an example in which edges are detected as characteristic portions from the secondary electron image while FIG. 8B is a view illustrating an example in which inflection points are detected as characteristic portions from the secondary electron image.

When the edges of the pattern of the design data 30 are detected as the characteristic portions, the second detection unit 16 detects edges 46*a*, 46*b*, 46*c*, and 46*d*, which extend in a width direction of patterns 41*a* and 41*b* of a secondary electron image 40, as the characteristic portions as illustrated in FIG. 8A.

Meanwhile, when the corners of the pattern of the design data 30 are detected as the characteristic portions, the second detection unit 16 detects inflection points 48*a*, 48*b*, 48*c*, and 48*d*, where the edges of the patterns 41*a* and 41*b* of the secondary electron image 40 start bending, as the characteristic portions as illustrated in FIG. 8B.

Here, the inflection points can be detected by methods described below.

Figure 9A:
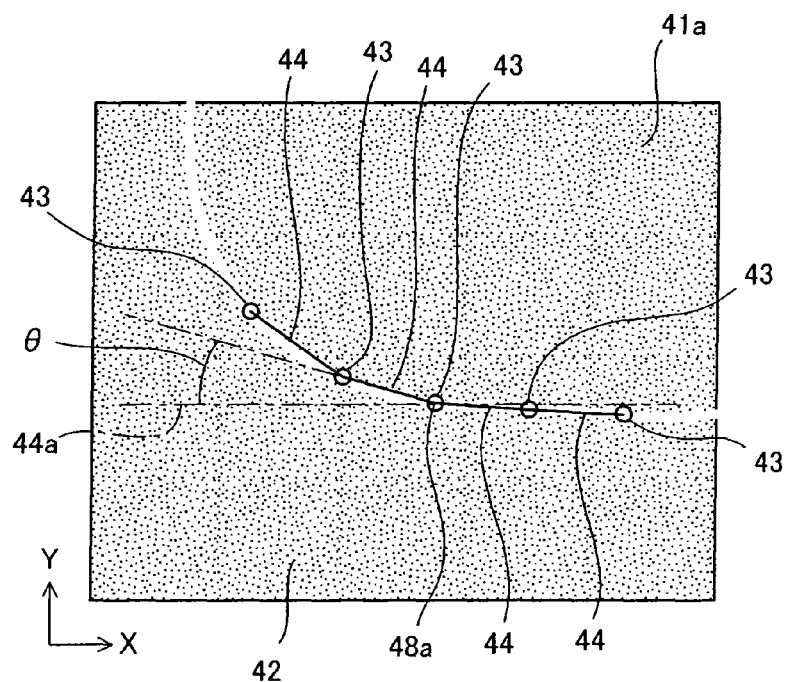
FIGS. 9A and 9B are views illustrating methods of detecting an inflection point according to the first embodiment.
Figure 9B:
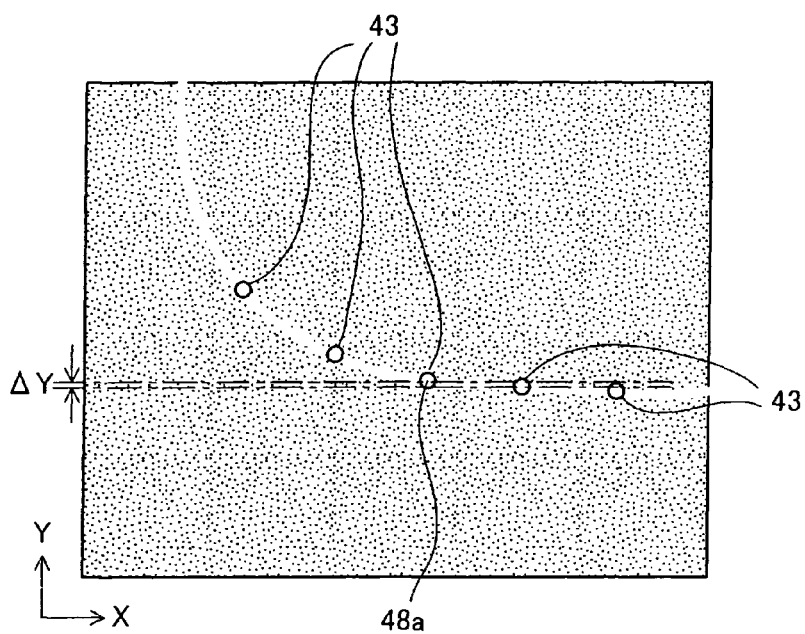

FIG. 9A is a view illustrating a method of detecting an inflection point based on edge angles and FIG. 9B is a view illustrating a method of detecting an inflection point based on the amount of change of an edge position in the width direction. Note that FIG. 9A and FIG. 9B correspond to a portion surrounded by a broken line N in FIG. 8B.

As illustrated in FIG. 9A, the second detection unit 16 arranges points 43 which overlap the edge of the pattern at intervals of constant pixels in the X direction. Next, a line segment 44 connecting each adjacent two points 43 is drawn and an angle θ formed between each line segment and a line 44*a* extending in the length direction (the X direction) is found. Then, the point 43 located adjacent to the line segment 44, which forms the angle θ exceeding a predetermined reference value, is detected as the inflection point 48*a*.

Alternatively, the inflection point may be found on the basis of the amount of change of an edge position in the width direction as illustrated in FIG. 9B.

In this case as well, the second detection unit 16 arranges the points 43 which overlap the edge of the pattern at intervals of constant pixels in the X direction. Next, an amount of change ΔY in the width direction (the Y direction) between each adjacent two points 43 is found. Then, the point 43 at which the amount of change ΔY exceeds a predetermined reference value is detected as the inflection point 48*a*.

The detection of the characteristic portion of the pattern in the secondary electron image with the second detection unit 16 is thus completed.

Next, in step S50 of FIG. 3, the alignment unit 17 (see FIG. 2) of the secondary electron image processor 13 positions and locates the measurement region in the secondary electron image based on a positional relationship between the characteristic portion of the pattern of the design data and the characteristic portion of the pattern of the secondary electron image.

Now, positioning of the measurement region will be concretely described below.

Figure 10A:
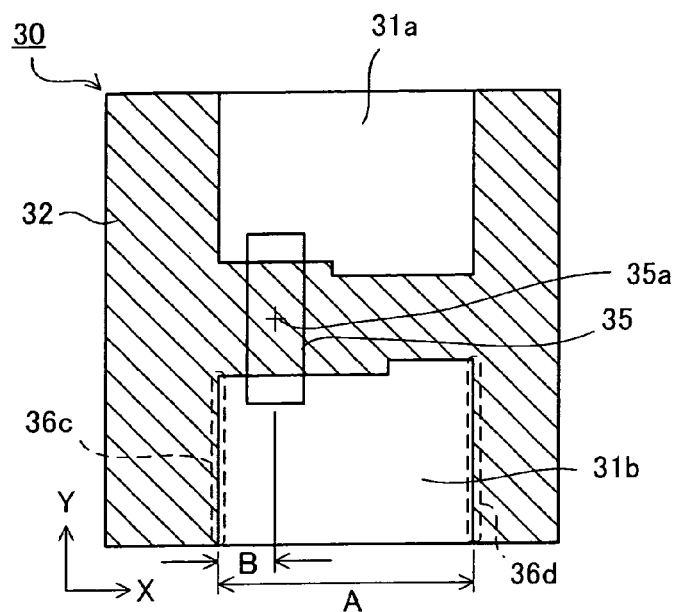
FIGS. 10A and 10B are views illustrating a method of positioning the measurement region in the secondary electron image by using two characteristic portions in the pattern measurement method according to the first embodiment.
Figure 10B:
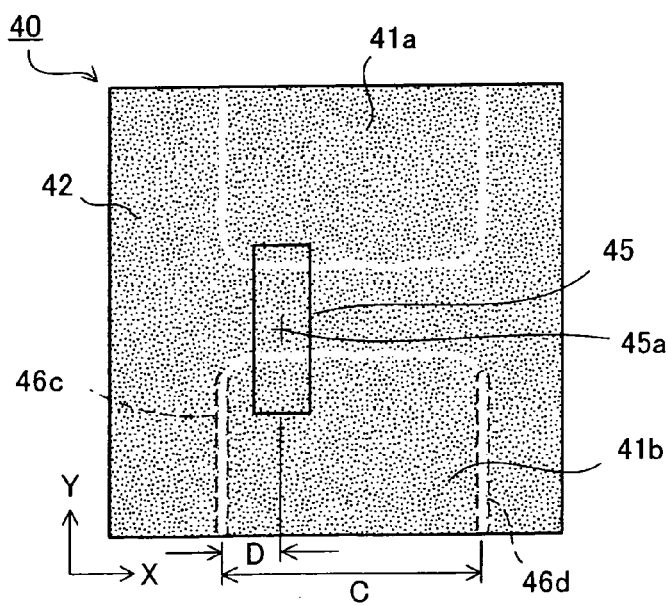

FIG. 10A is a view illustrating positions of the characteristic portions 36*c* and 36*d* as well as the measurement region 35 in the design data 30, and FIG. 10B is a view illustrating a method of positioning the measurement region in the secondary electron image with the alignment unit 17.

First, as illustrated in FIG. 10A, the alignment unit 17 refers to the design data 30 and extracts two characteristic portions which are distant in the length direction (the x direction) of the measurement region. Here, the two edges 36c and 36d are assumed to be extracted as the characteristic portions.

Next, the alignment unit 17 finds a distance A in the length direction (the X direction) between the two edges 36c and 36d. In addition, the alignment unit 17 finds a distance B in the length direction (the X direction) between the edge 36c of the edges 36c and 36d and the center 35a of the measurement region 35 and then finds a proportion B/A between the distance A and the distance B.

Next, as illustrated in FIG. 10B, the alignment unit 17 refers to the secondary electron image 40 and extracts the two edges 46c and 46d, which are the two characteristic portions corresponding to the characteristic portions of the pattern of the design data 30.

Subsequently, the alignment unit 17 finds a distance C between the edges 46c and 46d. Then, the alignment unit 17 determines a distance D between the center 45a of the measurement region 45 to be located and the edge 46c in such a manner as to satisfy a relational expression of B/A=D/C. A positional coordinate in the X direction of the center of the measurement region 45 in the secondary electron image is determined by adding the distance D thus found to an X-coordinate of the edge 46c. Positioning of the measurement region 45 in the length direction (the X direction) is thus completed.

The description has been given above for the case of positioning while focusing on the proportion between the distance A and the distance B as well as the proportion between the distance C and the distance D. Instead, it is possible to perform positioning while focusing on an offset amount between the distance A and the distance C as described below.

Specifically, a case will be considered in which the distance A (see FIG. 10A) between the edges in the design data is different from the distance C (see FIG. 10B) between the edges in the secondary electron image. In this case, an offset amount (C−A) between the distances is found by subtracting the distance A from the distance C. Next, the distance D (see FIG. 10B) in the secondary electron image is calculated by a formula (C−A)÷2+B. Then, an X-coordinate of the center of the measurement region 45 in the secondary electron image is calculated by adding the distance D thus found to the X-coordinate of the edge 46c.

Here, no error occurs in the measurement even when the position of the measurement region 45 is displaced in the width direction. Accordingly, positioning of the measurement region 45 in the width direction (the Y direction) is not performed in this embodiment and a Y-coordinate of the center 35a of the measurement region 35 of the design data is used without any change.

Thereafter, the alignment unit 17 locates a rectangular region, which has the center 45a as its center and has the same width and length as the measurement region 35, as the measurement region 45.

The procedures for positioning and locating the measurement region 45 are thus completed.

As described above, according to the method illustrated in FIG. 10A and FIG. 10B, the measurement region 45 is positioned on the basis of the positional relationship between the two characteristic portions distant in the length direction of the measurement region 35. Accordingly, it is possible to position and locate the measurement region 45 at high precision even when there are displacement and deviation in magnification between the design data 30 and the secondary electron image 40.

Depending on the shape of the pattern, there may be a case where only one characteristic portion is detectable from each of the design data and the secondary electron image. In this case, positioning will be performed in accordance with the following method.

Figure 11A:
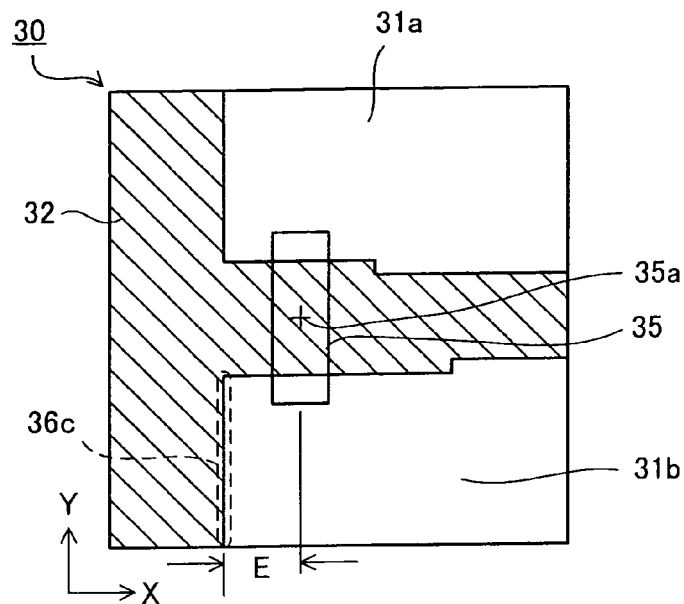
FIGS. 11A and 11B are views illustrating a method of positioning the measurement region in the secondary electron image by using one characteristic portion in the pattern measurement method according to the first embodiment.
Figure 11B:
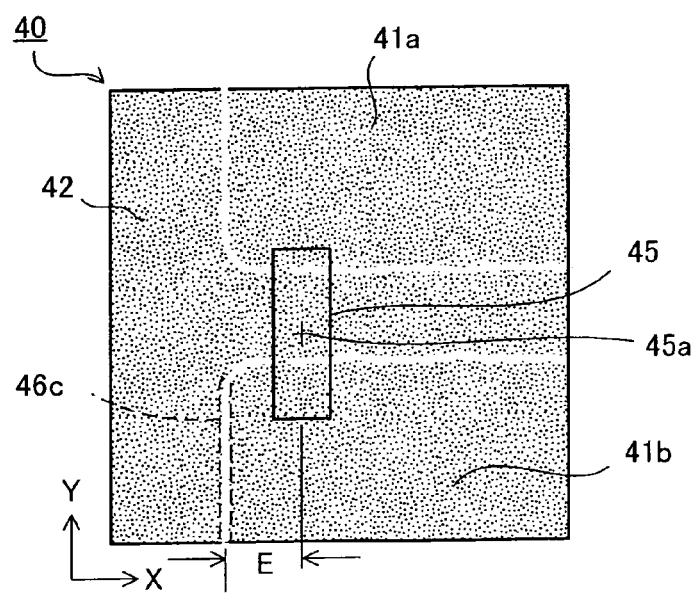

FIG. 11A is a view illustrating positions of the characteristic portion 36c and the measurement region 35 in the design data 30, and FIG. 11B is a view illustrating a method of positioning the measurement region using a single characteristic portion with the alignment unit 17.

Here, as illustrated in FIG. 11A, description is given of an example of positioning while using the edge 36c in the design data 30 as the characteristic portion. In this case, the alignment unit 17 finds a distance E in the length direction (the X direction) between the center 35a of the measurement region 35 and the edge 36c.

Next, as illustrated in FIG. 11B, the alignment unit 17 refers to the secondary electron image 40 and extracts the edge 46c which is the characteristic portion corresponding to the characteristic portion (the edge 36c) of the design data 30.

Subsequently, the alignment unit 17 calculates a positional coordinate in the length direction (the X direction) of the center 45a of the measurement region 45 in the secondary electron image 40 by adding the distance E to a coordinate in the length direction (the X direction) of the edge 46c.

Note that a positional coordinate in the width direction (the Y direction) of the center 45a of the measurement region 45 is defined as the same as a positional coordinate in the width direction (the Y direction) of the center 35a of the measurement region 35.

The above-described method enables positioning even in the case where only one characteristic portion is detectable.

The procedures for positioning and locating the measurement region in the secondary electron image with the alignment unit 17 in step S50 (see FIG. 3) are thus completed.

Although the case of using the edges as the characteristic portions has been described above as the example, the measurement region 45 can also be positioned with a similar method even when the corners and the inflection points of the pattern are defined as the characteristic portions.

The size of the measurement region to be located in the secondary electron image in the above-described step S50 is the same as the size of the measurement region defined in the design data. For this reason, the following problem may arise depending on the size of the measurement region.

Figure 12A:
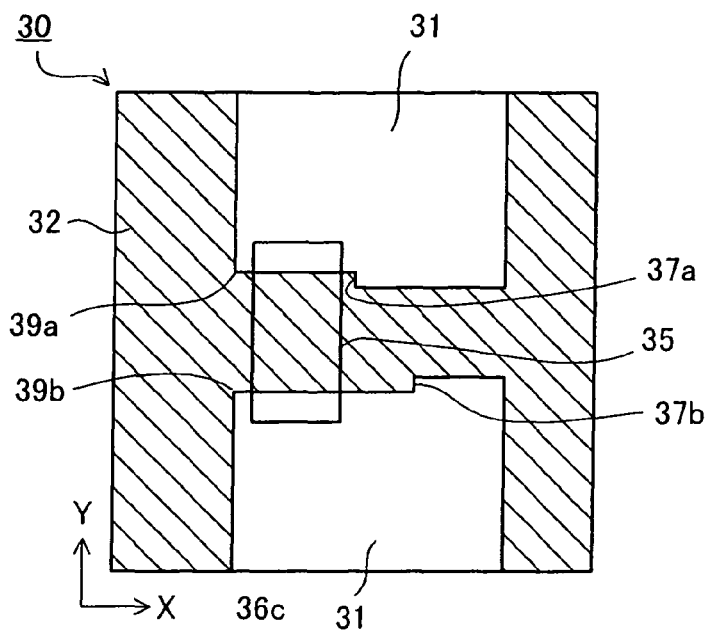
FIGS. 12A and 12B are views for explaining a problem in the case of not adjusting the length of the measurement region.
Figure 12B:
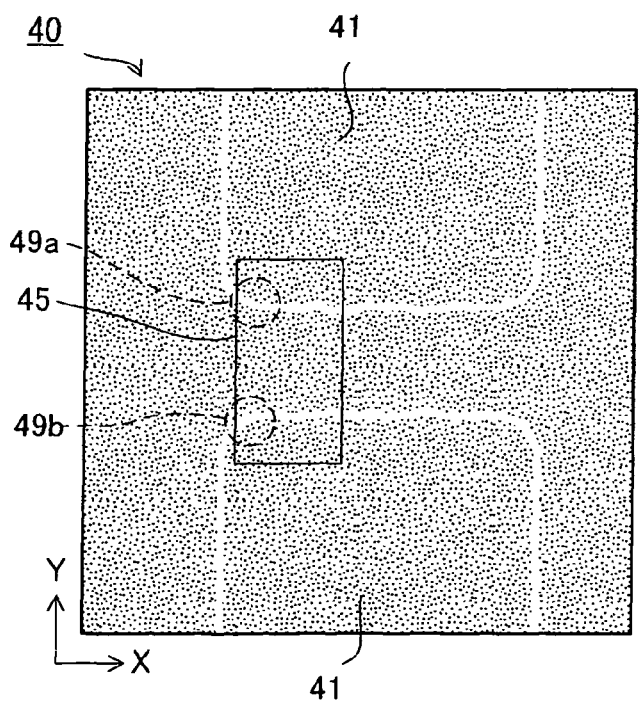

FIG. 12A is a view illustrating an example of the measurement region in the design data and FIG. 12B is a view illustrating an example of setting the measurement region in the secondary electron image to have the same size as the measurement region defined in FIG. 12A.

As illustrated in FIG. 12A, the measurement region 35 in the design data 30 is located so as not to include the corners 39a and 39b of the pattern 31.

However, corners 49a and 49b assume curvature when an actual pattern 41 is formed on the basis of the design data 30 as illustrated in the secondary electron image 40 of FIG. 12B. For this reason, if the measurement region 35 is too large or if the curvature of the corners 49a and 49b is large, rounded portions of the corners 49a and 49b may be included in the measurement region 45. As a consequence, measurement accuracy may be deteriorated as a width of a space 42 measured is larger than a real width, for example.

In this embodiment, the size adjustment unit 18 (see FIG. 2) of the secondary electron image processor 12 adjusts the size (length) of the measurement region in step S60 of FIG. 3 in order to avoid the above-described problem.

Figure 13A:
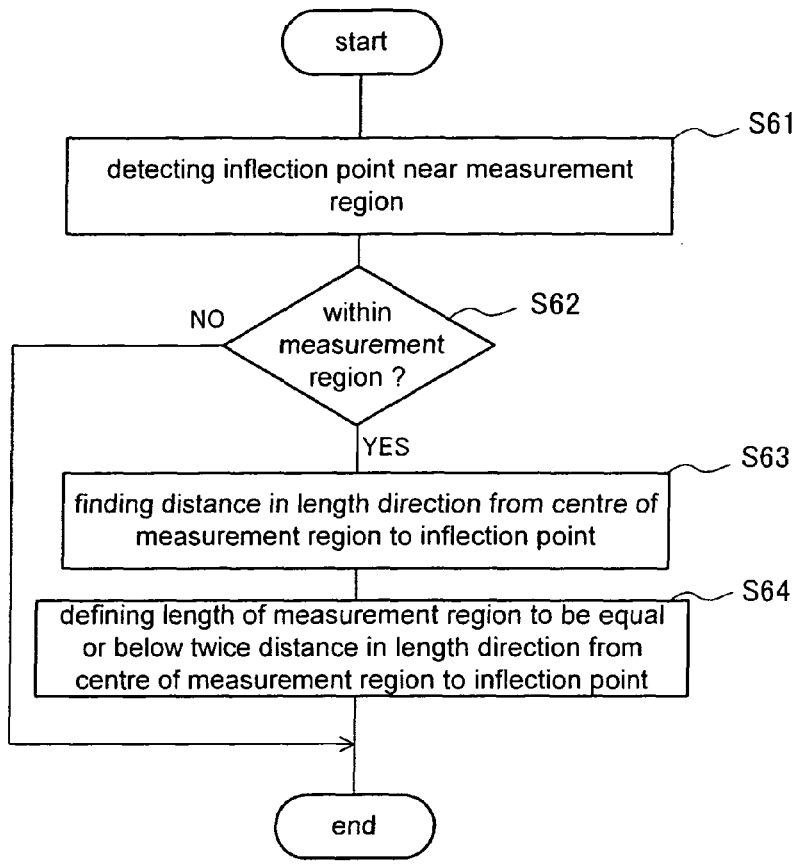
FIG. 13A is a flowchart illustrating a method of adjusting a size of the measurement region in the pattern measurement method according to the first embodiment and FIG. 13B is a view illustrating an example in which the size of the measurement region is adjusted by using the method of FIG. 13A.
Figure 13B:
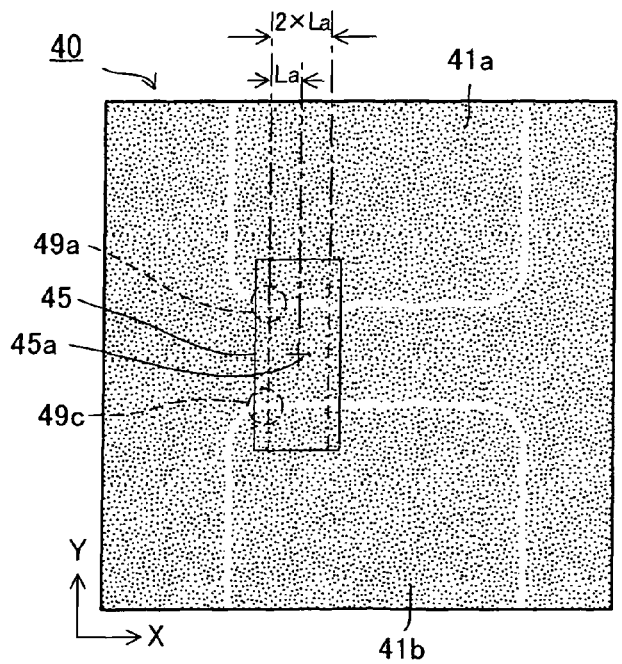

FIG. 13A is a flowchart illustrating a method of adjusting the size of the measurement region with the size adjustment unit 18 according to this embodiment and FIG. 13B is a view illustrating an example in which the size of the measurement region is adjusted by the method of FIG. 13A.

First, in step S61 of FIG. 13A, the size adjustment unit 18 refers to the secondary electron image and detects the inflection points of the corners near the measurement region. In the case of the secondary electron image 40 of FIG. 13B, for example, inflection points of the corners 49*a* and 49*b* are detected. Here, the inflection points are detected with the method described with reference to FIG. 9A and FIG. 9B.

Next, in step S62 of FIG. 13A, the size adjustment unit 18 checks whether or not an inflection point is included in the measurement region in the secondary electron image. When a judgment is made in step S62 that no inflection points are included in the measurement region (NO), the processing is terminated without carrying out the size adjustment of the measurement region.

On the other hand, when an inflection point is included in the measurement region (YES) in step S62, the processing goes to step S63 to carry out the size adjustment of the measurement region. In the case of FIG. 13B, the judgment of YES is made in step S62 as the inflection points of the two corners 49*a* and 49*b* are included in the measurement region.

Next, in step S63 of FIG. 13A, the size adjustment unit 18 finds a distance in the length direction to the inflection point located closest to the center of the measurement region. Specifically, a distance La in the length direction (the X direction in FIG. 13B) to the inflection point located closest to the center 45*a* of the measurement region 45 is found as illustrated in FIG. 13B.

Next, in step S64 of FIG. 13A, the size adjustment unit 18 defines the length of the measurement region to be equal to or below twice the distance in the length direction from the center of the measurement region to the inflection point. For example, as illustrated in FIG. 13B, the size adjustment unit 18 defines the length (the length in the X direction) of the measurement region 45 as 2×La, in which La is the distance from the center 45*a* of the measurement region 45 to the inflection point of the corner 49*a* (or the corner 49*b*).

Thus, the portions of the corners 49*a* and 49*b* assuming the curvature can be excluded from the measurement region 45.

With the above processes, the size adjustment of the measurement region 45 by the size adjustment unit 18 is completed.

Thereafter, in step S70 of FIG. 3, the measurement unit 19 of the secondary electron image processor 13 measures a line width of a pattern (or a space) in the measurement region 45.

Specifically, a line profile in the width direction is extracted from the measurement region 45 located in the secondary electron image 40. Here, line profiles are found at two or more portions located away from each other in the length direction of the measurement region in order to reduce an adverse effect attributed to asperity on the edge. Then, an averaged line profile is calculated by using the line profiles. Thereafter, the line width of the pattern is found by detecting a distance between local maximum values of luminance on the averaged line profile.

Thus, the measurement of the pattern using the pattern measurement apparatus 100 of this embodiment is completed.

As described above, in this embodiment, the measurement region is defined at the portion without a stepped portion by referring to the design data. Then, the measurement region is positioned and located in the secondary electron image on the basis of the positions of the characteristic portions of the pattern of the design data and the characteristic portions of the pattern of the secondary electron image.

Thus, even when there is deviation in the positional coordinates between the secondary electron image and the design data, it is possible to locate the measurement region precisely at the portion without the stepped portion in the secondary electron image.

In addition, the size adjustment unit 18 adjusts the size of the measurement region in such a manner as to exclude the inflection points near the corners from the measurement region. This can prevent the measurement region from including the stepped portions or the curved edge portions near the corners.

As a consequence, it is possible to locate the measurement region to include only a portion where the edge of the pattern is straight, and thereby to measure the line width of the pattern at high precision.

Second Embodiment

In the above-described first embodiment, an operator needs to manually designate the measurement object. Such an operation may be burdensome if there are numerous blocks serving as the measurement objects. In this regard, description will be given below of a method of designating measurement objects more simply when there are a plurality of measurement objects.

Figure 14:
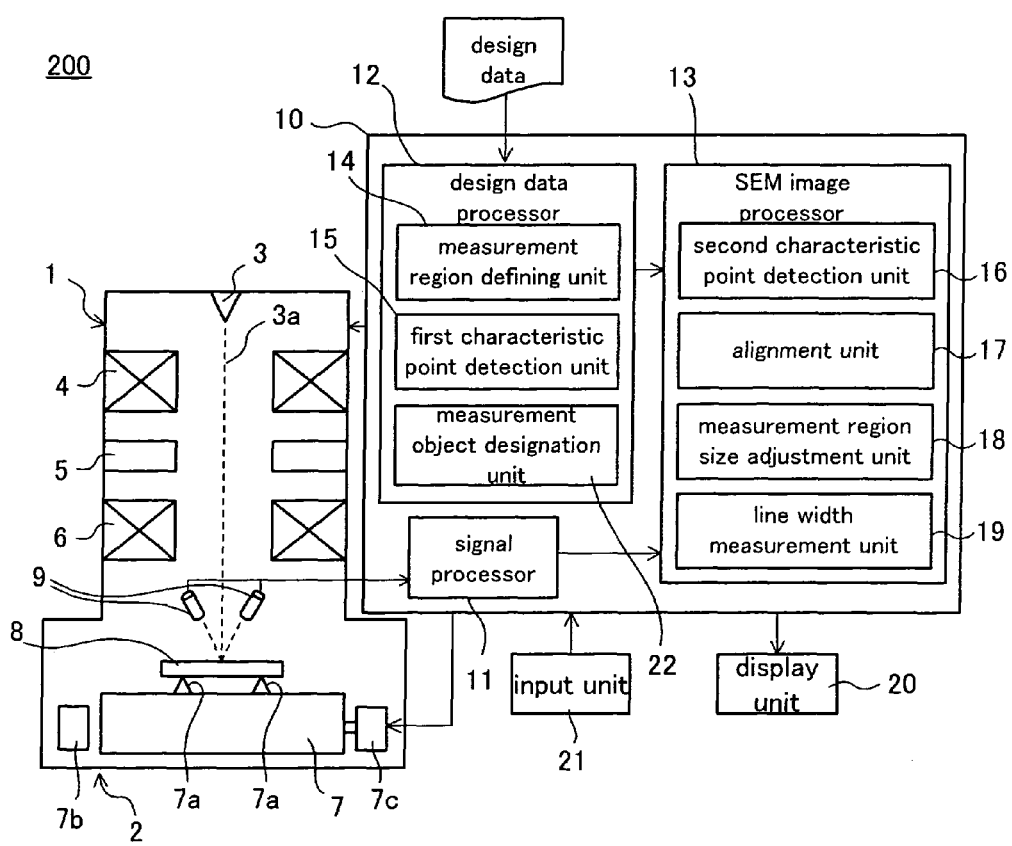
FIG. 14 is a block diagram illustrating a pattern measurement apparatus according to a second embodiment.

FIG. 14 is a block diagram illustrating a pattern measurement apparatus according to a second embodiment.

As illustrated in FIG. 14, a pattern measurement apparatus 200 of this embodiment is different from the pattern measurement apparatus 100 of FIG. 2 in that the design data processor 12 of the controller 10 further includes a measurement object designation unit 22. The rest of the configuration of the pattern measurement apparatus 200 is the same as the configuration of the pattern measurement apparatus 100. Thus, the same constituents will be denoted by the same reference numerals and description thereof will be omitted.

The measurement object designation unit 22 (see FIG. 14) of the pattern measurement apparatus 200 of this embodiment is configured to count the number of blocks sorted by the width and length, the blocks constituting patterns and spaces in design data, and to designate all the blocks having either a designated width or a designated length as the measurement objects.

Now, a method of causing the measurement object designation unit 22 to designate a measurement object according to this embodiment will be described below.

Figure 15:
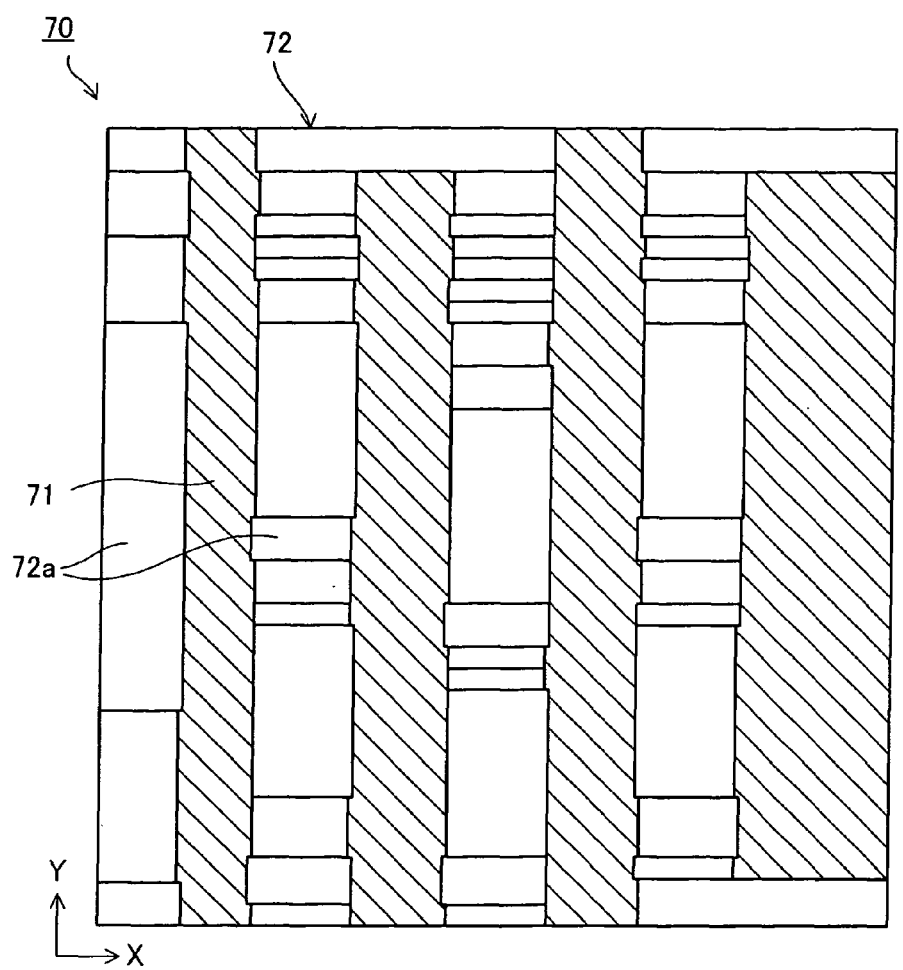
FIG. 15 is a view illustrating an example of design data.

FIG. 15 is a view illustrating an example of design data to be inputted to the design data processor 12 of the pattern measurement apparatus 200 of this embodiment. Here, description will be given of an example of inputting design data 70 as illustrated in FIG. 15 to the design data processor 12.

In FIG. 15, hatched portions represent patterns 71 while portions other than the hatched portions represent spaces 72. The spaces 72 are formed by connecting rectangular blocks 72*a*. Stepped portions in various sizes appear at joints of these blocks 72*a*.

Figure 16:
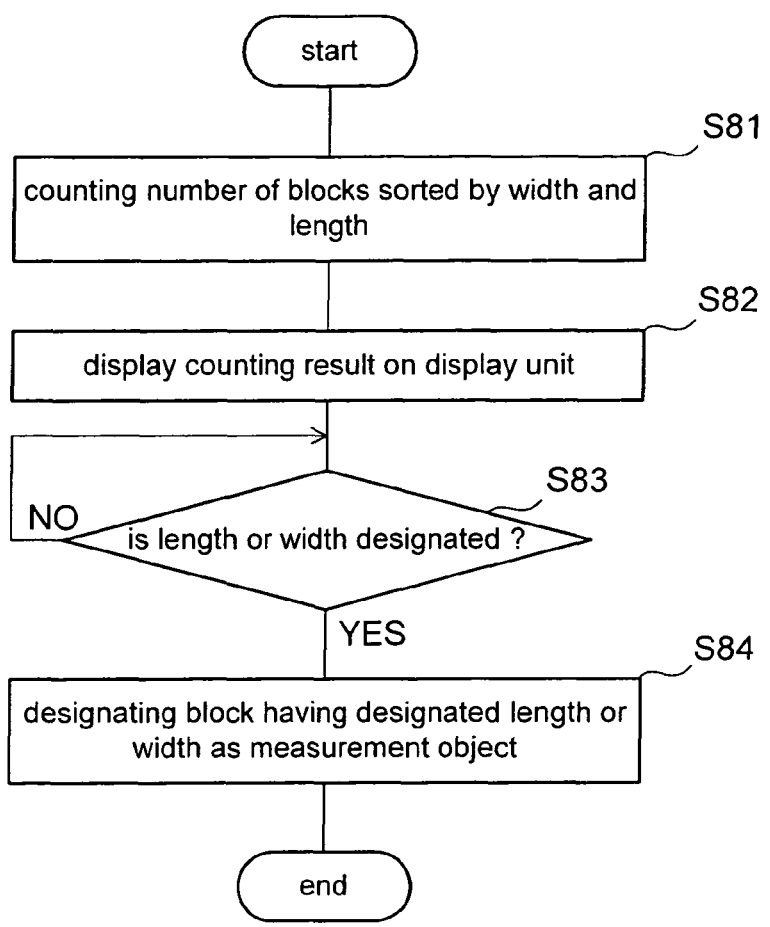
FIG. 16 is a flowchart illustrating a method of designating a measurement object according to the second embodiment.
Figures 17A, 17B:
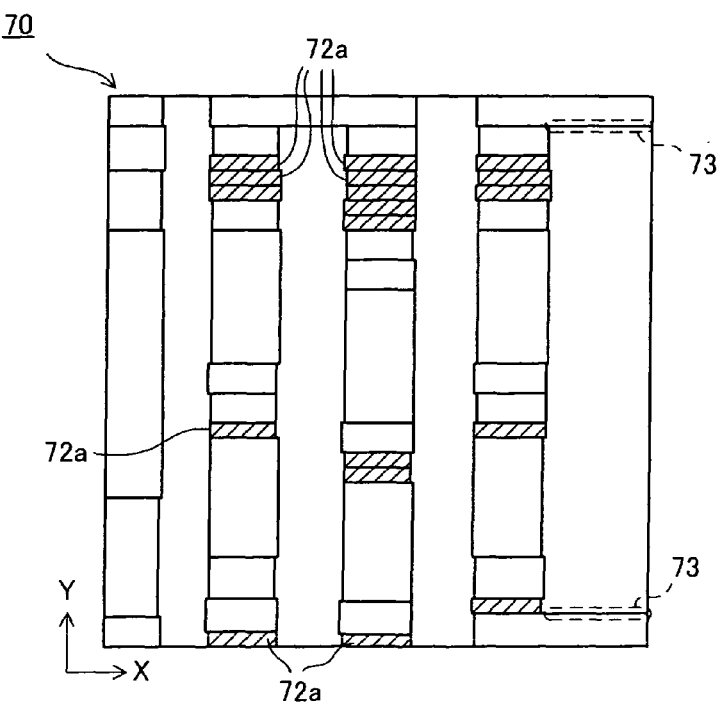
FIG. 17A is a table illustrating a result obtained by counting the number of blocks of design data and sorting the counted blocks based on widths and lengths by using a measurement object designation unit of the pattern measurement apparatus according to the second embodiment.
FIG. 17B is a view illustrating the blocks serving as the measurement objects when patterns having a length of 0.1 μm are selected on the basis of the table of FIG. 17A.

FIG. 16 is a flowchart illustrating a method of designating a measurement object by using the pattern measurement apparatus 200 of this embodiment. FIG. 17A is a table illustrating a result obtained by counting the blocks 72*a* included in the spaces 72 with the measurement object designation unit 22 of the pattern measurement apparatus 200 of this embodiment. FIG. 17B is a view illustrating an example in which the measurement objects are designated by the measurement objet designation unit 22.

As illustrated in FIG. 16, first in step S81, the measurement object designation unit 22 counts the number of blocks included in the spaces 72 and sorted by the width and length. Then, the measurement object designation unit 22 creates a table showing the numbers of blocks sorted by length and width as illustrated in FIG. 17A.

Next, in step S82, the measurement object designation unit 22 displays the table created in step S81 on the display unit 20 (see FIG. 14) of the pattern measurement apparatus 200.

In the case of a pattern (or a space) including many stepped portions such as an OPC mask, the shorter a pattern (or a space) is, the more difficult it is to create an actual pattern exactly according to design data. Accordingly, it is relatively important to manage line widths of shorter portions among the blocks.

In this regard, display of the result of counting the number of blocks included in the spaces 72 and sorted by the width and length as illustrated in FIG. 17A enables an operator to easily grasp blocks to be designated as measurement objects.

In the next step S83, the measurement object designation unit 22 awaits input of the length and width of the blocks by the operator.

The process goes to the next step S84 when the operator inputs the length (or the width) of the blocks to be designated as the measurement objects on the basis of the table (see FIG. 17A) displayed on the display screen of the display unit 20.

In step S84, the measurement object designation unit 22 designates all the blocks having the designated length or width as the measurement objects.

For example, when the blocks having a length of 0.1 µm are designated on the basis of the table of FIG. 17A, all the blocks 72a having the length of 0.1 µm in the design data 70 are included in the measurement objects as illustrated with hatched lines in FIG. 17B.

Thus, the procedures for designating the measurement objects by the measurement object designation unit 22 of this embodiment are completed.

Thereafter, in step S84, the line width of each of the blocks 72a, which are designated as the measurement objects in step S84, is measured by locating the measurement region 35 on the blocks 72a with the method described with reference to FIG. 3 to FIG. 13B. In this case, edges 73 of the design data 70 in FIG. 17B can be used as the characteristic portions for positioning the measurement regions.

As described above, according to this embodiment, a plurality of blocks having a prescribed length or width can be designated in a lump as the measurement objects by designating such a length or width. As a consequence, this embodiment allows designation of regions to be measured more promptly and simply as compared to the case of manually selecting the blocks one by one.

Third Embodiment

In a third embodiment, description will be given of a method of automatically designating a measurement object on the basis of the size of a stepped portion of a pattern.

A pattern measurement apparatus used in this embodiment is similar to the pattern measurement apparatus 200 (the second embodiment) illustrated in FIG. 14 and a style of the design data is also similar to that of FIG. 15. Hence, description of the apparatus and the data will be omitted.

Figure 18:
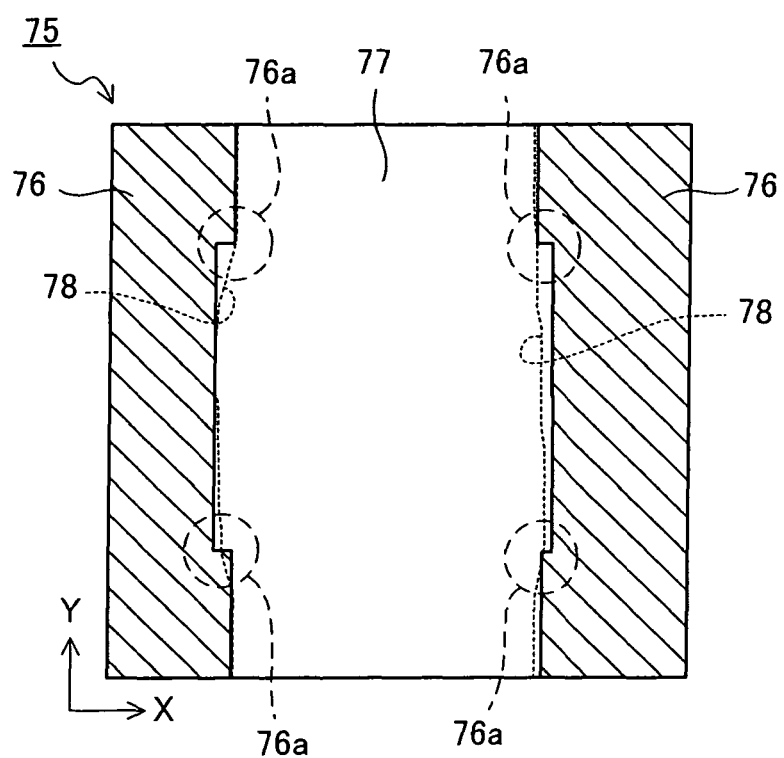
FIG. 18 is a view illustrating edges in design data and in an actual pattern near stepped portions.

FIG. 18 is a view illustrating a portion of design data in which a pattern contains large stepped portions, and illustrating edge positions of an actually created pattern in this portion.

In FIG. 18, hatched portions represent patterns 76 in design data 75. A space 77 is formed between the patterns 76. Stepped portions 76a are formed in the patterns 76.

Meanwhile, broken lines in FIG. 18 indicate positions of edges 78 of the pattern actually created on the basis of the design data. As illustrated in the drawing, a gap between the position of the edge in the design data and the position of the edge 78 of the actually created pattern is increased in the vicinity of each of the relatively large stepped portions 76a.

For this reason, it is important to manage the line width of the pattern in the vicinity of each relatively large stepped portion 76a in order to create a mask pattern at high precision.

Accordingly, in this embodiment, a stepped portion having a size equal to or above a given reference value is detected in the design data and a block in the vicinity of the detected stepped portion is designated as a measurement object, as described below.

Figure 19:
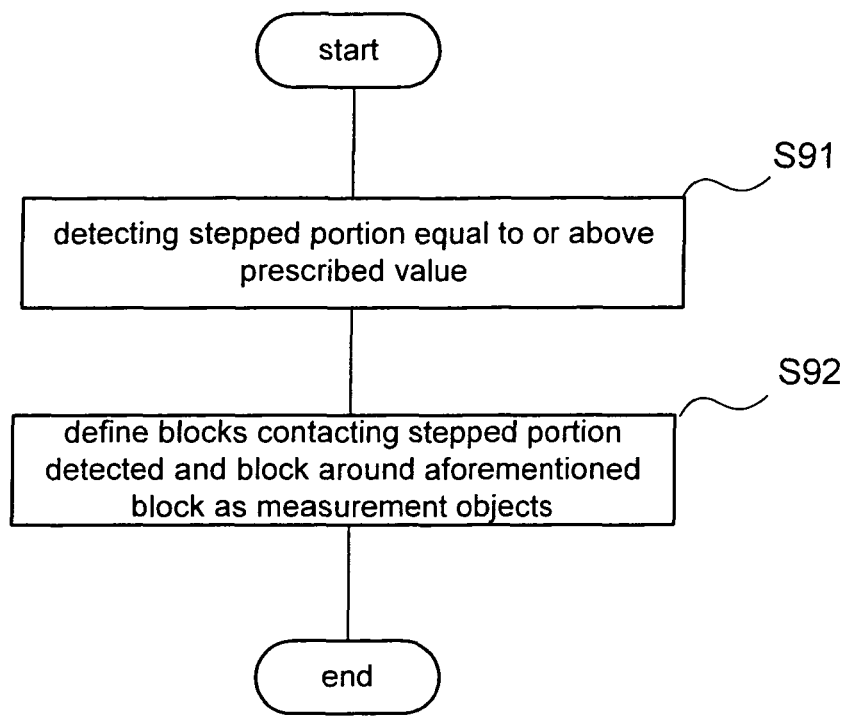
FIG. 19 is a flowchart illustrating a method of designating a measurement object in a pattern measurement method according to a third embodiment.
Figure 20A:
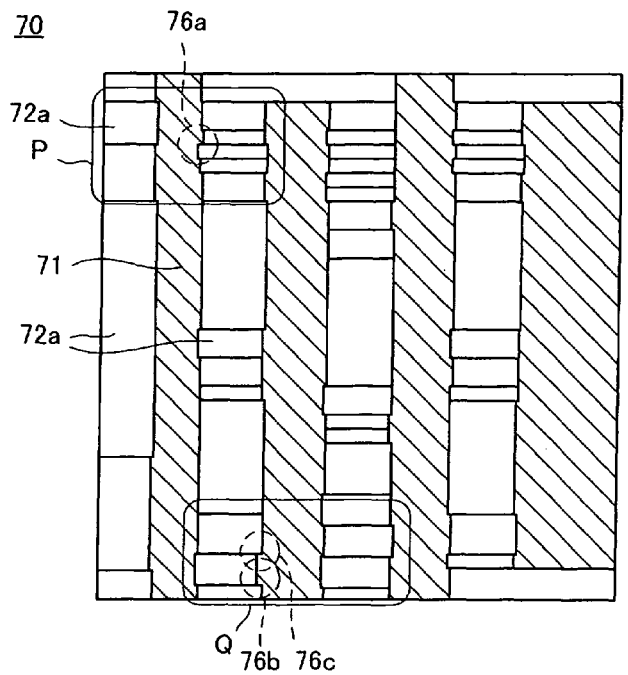
FIGS. 20A to 20C are views illustrating a method of designating a measurement object according to the third embodiment.
Figure 20B:
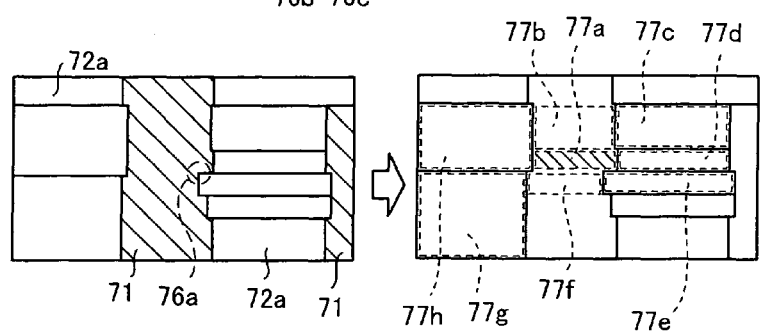
Figure 20C:
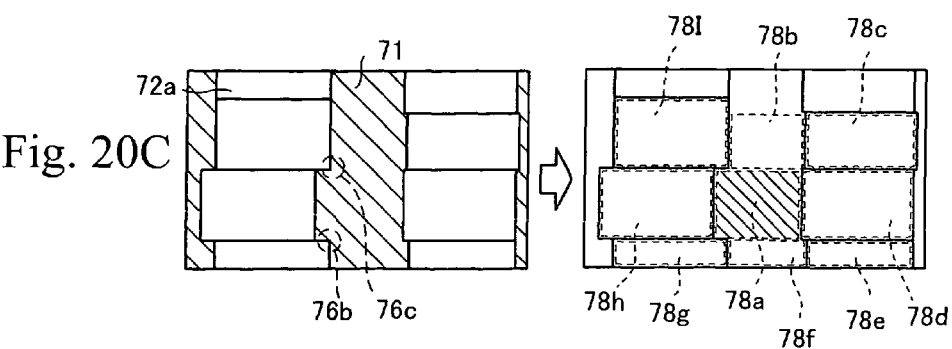

FIG. 19 is a flowchart illustrating a method of designating a measurement object in a pattern measurement method of this embodiment. FIG. 20A is a view illustrating an example of stepped portions detected by the method of FIG. 19. FIG. 20B and FIG. 20C are views illustrating the method of designating the measurement objects in a region P and a region Q in FIG. 20A, respectively.

First, in step S91 of FIG. 19, the measurement object designation unit 22 (see FIG. 14) of the pattern measurement apparatus 200 detects stepped portions having the size equal to or above a prescribed value in the design data. Here, the stepped portions having the size equal to or above 25 nm are detected, for example.

In the case of design data 70 illustrated in FIG. 20A, stepped portions 76a, 76b, and 76c are detected as the stepped portions having the size equal to or above the prescribed value.

Next, in step S92 of FIG. 19, the measurement object designation unit 22 designates blocks located adjacent to edges of the stepped portions 76a, 76b, and 76c thus detected, and blocks located around the aforementioned blocks, collectively as the measurement objects.

As illustrated in FIG. 20B, in the region P, a block 77a located adjacent to an edge of the detected stepped portion 76a is designated as the measurement object. Subsequently, blocks 77c to 77h located around the block 77a are additionally designated as the measurement objects.

As illustrated in FIG. 20C, in the region Q, a block 78a located adjacent to edges of the stepped portions 76b and 76c is designated as the measurement object. Subsequently, blocks 78b to 78l located around the block 78a are additionally designated as the measurement objects.

As described above, according to this embodiment, the blocks located adjacent to the relatively large stepped portion, which is more likely to cause deviation in the line width, and the blocks located around the aforementioned blocks can collectively be designated as the measurement objects. Thus, in an OPC mask including numerous stepped portions, the regions whose line widths need to be managed can automatically be designated as the measurement objects.

What is claimed is:
1. A pattern measurement apparatus comprising:
    an electron beam irradiation unit configured to irradiate a surface of a sample with an electron beam;
    a detector configured to detect secondary electrons generated on the surface of the sample;

a signal processor configured to create a secondary electron image of the surface of the sample based on a detection signal from the detector;

a measurement region definition unit configured to define a measurement region in design data while referring to the design data for the sample;

a first detection unit configured to detect a characteristic portion of the design data;

a second detection unit configured to detect a characteristic portion of the secondary electron image;

an alignment unit configured to position and locate the measurement region of the design data in the secondary electron image based on a positional relationship between the characteristic portion of the design data and the characteristic portion of the secondary electron image; and a measurement unit configured to measure a width of a pattern based on positions of edges of the pattern inside the measurement region of the secondary electron image.

2. The pattern measurement apparatus according to claim 1, wherein each of the first detection unit and the second detection unit detects an edge extending in a measurement direction of the corresponding measurement region as the characteristic portion.

3. The pattern measurement apparatus according to claim 1, wherein
the first detection unit detects a corner of a pattern in the design data as the characteristic portion, and
the second detection unit detects an inflection point of an edge of the pattern in the secondary electron image as the characteristic portion.

4. The pattern measurement apparatus according to claim 1, wherein the alignment unit positions the measurement region based on a positional relationship of two characteristic portions of the design data with two corresponding characteristic portions of the secondary electron image.

5. The pattern measurement apparatus according to claim 1, further comprising a size adjustment unit configured to, when the inflection point of the edge of the pattern is included in the measurement region located in the secondary electron image, adjust a length of the measurement region to be equal to or below twice a distance from the center of the measurement region to the inflection point.

6. The pattern measurement apparatus according to claim 1, wherein the measurement region definition unit locates the measurement region at a portion of the pattern of the design data, the portion having no stepped portion causing a change in a line width.

7. The pattern measurement apparatus according to claim 1, wherein
the design data comprises a pattern and a space each formed of a plurality of divided rectangular blocks, and
the apparatus further comprises a measurement object designation unit configured to designate blocks having any of a predetermined length and a predetermined width among the blocks in the design data in a lump as measurement objects in which the measurement region is defined.

8. The pattern measurement apparatus according to claim 1, wherein
the design data comprises a pattern and a space each formed of a plurality of divided rectangular blocks, and
the apparatus further comprises a measurement object designation unit configured to detect a stepped portion having a size equal to or above a prescribed value from the design data and to designate a block adjacent to the detected stepped portion and blocks located around the adjacent block as measurement objects in which the measurement region is defined.

9. A pattern measurement method for defining a measurement region in a secondary electron image and finding a line width of a pattern in the measurement region using positions of edges of the pattern, the method comprising the steps of:
defining a measurement region in design data corresponding to a field of view of the secondary electron image;
detecting a characteristic portion of the design data;
detecting a characteristic portion of the secondary electron image; and
positioning and locating the measurement region of the design data in the secondary electron image based on a positional relationship between the characteristic portion of the design data and the characteristic portion of the secondary electron image.

10. The pattern measurement method according to claim 9, wherein each of the characteristic portion of the design data and the characteristic portion of the secondary electron image is an edge of a pattern extending in a measurement direction of the measurement region.

11. The pattern measurement method according to claim 9, wherein
the characteristic portion of the design data is a corner of a pattern in the design data, and
the characteristic portion of the secondary electron image is an inflection point of the edge of the pattern in the secondary electron image.

12. The pattern measurement method according to claim 9, wherein the measurement region is positioned on the basis of a positional relationship of two characteristic portions of the design data with two corresponding characteristic portions of the secondary electron image.

13. The pattern measurement method according to claim 9, further comprising the step of, when the inflection point of the edge of the pattern is included in the measurement region located in the secondary electron image, adjusting a length of the measurement region to be equal to or below twice a distance from the center of the measurement region to the inflection point.

14. The pattern measurement method according to claim 9, wherein the measurement region is located at a portion of the pattern of the design data, the portion having no a stepped portion causing a change in a line width.

15. The pattern measurement method according to claim 9, wherein
the design data comprises a pattern and a space each formed of a plurality of divided rectangular blocks, and
the method further comprises the step of designating blocks having any of a predetermined length and a predetermined width among the divided rectangular blocks in the design data in a lump as measurement objects in which the measurement region is defined.

16. The pattern measurement apparatus according to claim 9, wherein
the design data comprises a pattern and a space each formed of a plurality of divided rectangular blocks, and
the apparatus further comprises the steps of:
detecting a stepped portion having a size equal to or above a prescribed value from the design data; and
designating a block located adjacent to the detected stepped portion and blocks located around the adjacent block as measurement objects in which the measurement region is defined.

* * * * *